United States Patent [19]

Hellstrom et al.

[11] Patent Number: 5,091,178

[45] Date of Patent: Feb. 25, 1992

[54] TUMOR THERAPY WITH BIOLOGICALLY ACTIVE ANTI-TUMOR ANTIBODIES

[75] Inventors: Karl E. Hellstrom; Ingegerd Hellstrom, both of Seattle, Wash.

[73] Assignee: Oncogen, Seattle, Wash.

[21] Appl. No.: 473,137

[22] Filed: Jan. 30, 1990

Related U.S. Application Data

[63] Continuation of Ser. No. 831,684, Feb. 21, 1986, abandoned.

[51] Int. Cl.$^5$ .................... A61K 39/395; C07K 15/28
[52] U.S. Cl. .................... 424/85.8; 424/85.91; 424/88; 530/387; 530/388; 530/389; 530/391; 530/808; 530/828; 435/240.27; 514/2; 514/8; 514/21
[58] Field of Search .................... 424/85.8, 85.91, 93; 530/387, 388, 389, 390, 395, 806, 808, 828; 435/240.27, 172.2, 70.21

[56] References Cited

U.S. PATENT DOCUMENTS

| | | | |
|---|---|---|---|
| 4,146,603 | 3/1979 | Davidson et al. | 424/85.8 |
| 4,361,549 | 11/1982 | Kung et al. | 424/85.8 |
| 4,444,744 | 4/1984 | Goldenberg | 424/85.8 |
| 4,579,827 | 4/1986 | Sakamoto et al. | 424/85.8 |
| 4,650,756 | 3/1987 | Old et al. | 530/387 |
| 4,661,347 | 4/1987 | Muller-Eberhard et al. | 424/85 |
| 4,661,586 | 4/1987 | Leny et al. | 530/387 |
| 4,675,287 | 6/1987 | Reisfeld et al. | 424/85.8 |
| 4,693,966 | 9/1987 | Houghton et al. | 530/387 |
| 4,714,613 | 12/1987 | Shouval et al. | 424/85.8 |
| 4,939,240 | 7/1990 | Chu et al. | 424/85.8 |

FOREIGN PATENT DOCUMENTS

0162825 11/1985 European Pat. Off.

OTHER PUBLICATIONS

Young et al., Science, 211, 487-9 (1981).
Dippold et al., Conser. Res. 44(2) 1984 pp. 806-810.
Cheresh et al., PNAS 82(15) pp.5/55-5/59, 1985 (abst. CA).
Chany et al., CA vol. 103, 1985, #20951j.
Young et al., CA vol. 94, 1981, #101209W.
Ito et al., CA vol. 102, 1985, #76880y.
Katano, CA vol. 101, 1984, #189449.
Herlyn et al., Env. J. Immunol., 1979, 9, pp. 657-659.
Manson et al., Biochemica Biophysica Acta 1985, 834, pp. 110-116.
Nilsson et al., Biochimica Biophysica Acta 1985, pp. 577-583.
Lundholm et al., Int Archs Allergy Appl Immun 71, 1983, pp. 178-181.
Maymani et al., Science 212 1981 pp. 55-56.
Nakeinz, J. Leukoyta Biol., 35(1), 1984, pp. 131-139 (abst).
Imai et al., Scond. J Immunol 14(4), 1981, pp. 369-377 (abst).
Kawase et al., Conser Res 45(4), 1985, pp. 1663-1668 (abst).
Hellstrom et al., 1985, Proc. Natl. Acad. Sci. 82:1499-1502.
Hellstrom et al., 1985, Monoclonal Antibodies and Cancer Therapy, USCLA Symp. on Molec. and Cell. Biol., Alan R. Liss) pp. 149-164.
Hellstrom and Hellstrom in Accomplishments in Cancer Research 1985, 194:216-240 (J. F. Fortner, J. E. Rhoads, J. B. Lippincott. Co.).
Hellstrom et al., 1984, Contrib. to Oncol. Series: Genes and Antigens in Cancer Cells (Reithmuller, Koprowski, Van Kliest & Munk), pp. 121-131.
Burchell et al. in Monoclonal Antibodies for Tumor Detection and Drug Targeting (R. W. Baldwin & V. S. Byers, Acad. Press, 1985) pp. 1-15.
Hakomori, 1984, Ann. Rev. Immunol., 2:103-126.
Nepom, 1984, Proc. Natl. Acad. Sci., 81:2864-2867.
Koprowski et al., 1984, Proc. Natl. Acad. Sci., 81:216-219.
Hellstrom et al., 1983, J. Immunol., 130:1467-1472.
Nudelman et al., 1982, J. Biol. Chem., 257:12752-12756.
Brown et al., 1981, J. Immunol., 127:539-546.
Colcher et al., 1981, Cancer Res., 41:1451-1459.
Woodbury et al., 1980, Proc. Natl. Acad. Sci., 77:2183-2186.
Schulz et al., 1983, Proc. Natl. Acad. Sci., 80:5407-5411.
Fidler and Poste, 1982, Springer Semin. Immunopathol. 5:161-174.
Hellstrom et al., 1981, Int. J. Cancer, 27:281-285.
Uananue and Benacerraf, 1984, Text. Immunol. (Williams & Wilkins, Chapter (12)), pp. 218-238.
Cerrottini et al., 1974, Adv. Immunol., 18:67-132.
Julius et al., 1973, Eur. J. Immunol., 3:645-649.
Pollack et al., 1972, Int. J. Cancer, 9:316-323.
Skurzak et al., 1972, J. Exp. Med. 135:997-1102.
MacLennan et al., 1969, Immunol. 17:897-910.
Perlmann et al., 1969, Adv. Immunol. 11:117-193.
Hellstrom et al., 1965, Progr. Allergy 9:158-245.
Rowland et al., 1985, Cancer. Immunol. Immunother., 19:1-7.
DeNardo et al., 1985, Int. J. Radiation Oncology Biol. Phys., 11:335-348.
Kemshead in Monoclonal Antibodies for Tumor Detection and Drug Targeting (R. W. Baldwin & V. S. Byers, Academic Press, 1985) pp. 281-302.

(List continued on next page.)

Primary Examiner—Esther L. Kepplinger
Assistant Examiner—Jeff Kughan
Attorney, Agent, or Firm—Pennie & Edmonds

[57] ABSTRACT

A method for identifying and using antibodies which are directed against tumor-associated glycolipid antigens and which are capable of activating serum complement or antibody dependent cellular cytotoxicity. These antibodies find use in the therapy of tumors. Administration of the antibodies results in lysis of the tumor cells in vivo.

3 Claims, No Drawings

Vitetta and Uhr, 1984, Transplant., 37:535–538.
Order, 1984, Comp. Ther. 10:9–18.
Carrasquillo et al., 1984, Cancer Treatment Reports, 68:317–328.
Larson et al., 1983, J. Clin. Invest. 72:2101–2114.
Yeh et al., 1982, Int. J. Cancer, 29:269–275.
Garrigues et al., 1982, Int. J. Cancer, 29:511–515.
Jansen et al., 1982, Immunol. Rev., 62:185–216.
Brown et al., 1981, Proc. Natl. Acad. Sci., 78:539–543.
Brown et al., 1979, J. Immunol. Meth., 31:201–209.
Hurwitz et al., 1975, Cancer Res., 35:1175–1181.
Ghose et al., 1972, Brit. Med. J., 3:495–499.
Cole et al., 1985, in Monoclonal Antibodies and Cancer Therapy (Alan R. Liss) pp. 77–96.
Takeda et al., 1985, Nature, 314:452–454.
Neuberger et al., 1984, Nature, 312:604–608.
Morrison et al., 1984, Proc. Natl. Acad. Sci., 81:6851–6855.
Cote et al., 1983, Proc. Natl. Acad. Sci., 80:2026–2030.
Ey et al., 1978, Immunochemistry, 15:429–436.
Kohler & Milstein, 1975, Nature, 256:495–497.ph 05091178

TUMOR THERAPY WITH BIOLOGICALLY ACTIVE ANTI-TUMOR ANTIBODIES

This is a continuation of application Ser. No. 831,684, filed Feb. 21, 1986, now abandoned.

1. FIELD OF THE INVENTION

The present invention involves antibodies that are (a) directed against glycolipid antigens on the surface of tumor cells, and (b) capable of activating complement and/or mediating an antibody-dependent cellular cytotoxicity resulting in the lysis of the tumor cells to which the antibodies bind. The antibodies of the present invention can be used in the treatment of tumors.

2. BACKGROUND OF THE INVENTION

2.1. Tumor Cell Antigens and Anti-tumor Antibodies

Tumor cells express certain antigens which are absent from, or present in small amounts on, their normal cellular counterparts. Most of these are differentiation antigens, shared by the tumor and certain embryonic cells. Some of the antigens that appear with sufficient selectivity in tumors may serve as possible targets for therapeutic agents. This has been recently reviewed for malignant melanoma, which is one of the human tumors most studied in this respect (Hellstrom and Hellstrom, in Accomplishments in Cancer Research-194 Prize Year, General Motors Cancer Research Foundation, J. G. Fortner & J. E. Rhoads, eds., J. B. Lippincott Company, Philadelphia 1985, p 216-240, as well as for other tumors (Burchell and Taylor-Papadimitriou, in R. W. Baldwin and V. S. Byers, eds., Monoclonal Antibodies for Tumor Detection and Drug Targeting, Academic Press, 1985, pp. 1-15; Kemshead, ibid, pp. 281-302).

Many antibodies have been made to cell surface antigens that are expressed in greater quantities by human tumors than by normal tissues. It has also been well established that antibodies to cell surface antigens can be cytotoxic to tumor cells in the presence of complement (Hellstrom et al., 1962, Progr. Allergy 9: 158-245), and that some antibodies can mediate antibody-dependent cellular cytotoxicity (Perlmann et al., 1969, Adv. Immunol. 11: 117-193; MacLennan et al., 1969, Immunol. 17: 897-910; Skurzak et al., 1972, J. Exp. Med. 135: 997-1002; Pollack et al., 1972, Int. J. Cancer, 9: 316-323). In the first case, an appropriate source of complement (generally rabbit or guinea pig), and in the latter case a source of effector cells (generally of mouse origin) is needed.

The evidence that antibodies to tumor-associated antigens can kill human tumor cells in the presence of human effector cells is more recent (Hellstrom et al., 1981, Int. J. Cancer 27: 281-285; as is the evidence that antibodies to such antigens can kill tumor cells in the presence of human serum as a source of complement (Hellstrom et al., 1985, Proc. Natl. Acad. Sci. 82: 1499-1502; Hellstrom et al., 1985, Monoclonal Antibodies and Cancer Therapy, USCLA Symposia on Molecular and Cellular Biology, Vol. 27, pp.149-164 Alan R. Liss, Inc., N.Y.).

2.3. Therapeutic Uses of Anti-tumor Antibodies as Carriers of Radioisotopes, Toxins or Drugs Attractive approaches for preparing anti-cancer agents involve labeling antibodies with radioactive isotopes (Larson et al., 1983, J. Clin. Invest. 72: 2101-2114; Order, 1984, Compr. Ther. 10: 9-18; Carrasquillo et al., 1984, Cancer Treatment Reports 68: 317-328; de Nardo et al. 1985, Int. J. Radiation Oncology Biol. Phys. 11: 335-348), or conjugating antibodies to toxins (Jansen et al., 1982, Immunol. Rev. 62: 185-216; Vitetta and Uhr, 1984, Transplant. 37: 535-538) or anti-cancer drugs Ghose et al., 1972, Brit. Med. J. 3: 495-499; Hurwitz et al., 1975, Cancer Res. 35: 1175-1181; Rowland et al., 1985, Cancer Immunol. Immunother. 19: 1-7). The antibody gives the specificity and the isotope or drug provides the ability to destroy the tumor. However, a disadvantage of this approach is the fact that both anti-cancer drugs and radioisotopes have a high level of toxicity to normal tissues. Thus, nonspecific uptake in various organs such as kidney, liver, or bone-marrow could lead to substantial side-effects.

3. SUMMARY OF THE INVENTION

The present invention is related to antibodies which are directed to glycolipid antigens at the surface of tumor cells and which belong to a class of immunoglobulin capable of activating serum complement and/or mediating antibody dependent cellular cytotoxicity by human effector cells. The antibodies of the present invention can lyse the tumor cells expressing these antigens both in vitro and in vivo.

The invention is also directed to methods for treating tumors in vivo using the antibodies of the present invention as therapeutic agents. After administration in vivo, the antibodies of the present invention should bind preferentially to the tumor cells which express the glycolipid antigen. Upon binding to the tumor cell, either serum complement will be activated or antibody dependent cellular cytotoxicity will be mediated resulting in lysis of the tumor cells.

The method of the present invention offers several advantages over techniques which involve the use of antibody-conjugates, because radioisotopes and/or toxins, which may exhibit a high level of toxicity to normal tissues, are not required. Moreover, nonspecific uptake of the unmodified antibody molecules of the present invention by normal tissues should result in minimizing side-effects of the therapy.

3.1. Definitions

The terms listed below will have the meanings indicated:

ADCC=antibody dependent cellular cytotoxicity

4. DETAILED DESCRIPTION OF THE INVENTION

The present invention involves a method based on the use of antibodies which are (a) directed against tumor-associated glycolipid antigens, and (b) belong to a subclass or isotype that is capable of mediating the lysis of tumor cells to which the antibody molecule binds. More specifically, these antibodies should belong to a subclass or isotype that, upon complexing with the glycolipid tumor-associated antigen, activates serum complement and/or mediates antibody dependent cellular cytotoxicity (ADCC) by activating effector cells such as natural killer cells or macrophages.

The present invention is also directed to the use of these antibodies, in their native form, for therapy of human tumors. For example, many IgG2a and IgG3 mouse antibodies which identify tumor-associated cell surface glycolipid antigens can be used in vivo for tumor therapy. In fact, since many tumor-associated glycolipid antigens exist (Hakomori, 1984, Ann. Rev. Immunol. 2: 103-126), and some antibodies, like L6 described herein, react with a large spectrum of human tumors, the antibodies and their therapeutic use have general applicability.

4.1. Characteristics of the Antibody Molecules of the Invention

Biological activity of antibodies is known to be determined, to a large extent, by the Fc region of the antibody molecule (Uanue and Benacerraf, 1984, Textbook of Immunology, 2nd Edition, Williams & Wilkins, Ch. 12 pp. 218-238). This includes their ability to activate complement and to mediate antibody-dependent cellular cytotoxicity (ADCC) as effected by natural killer cells or macrophages. Antibodies of different classes and subclasses differ in this respect, and, according to the present invention, antibodies of those classes having the desired biological activity should be selected. For example, mouse immunoglobulins of the IgG3 and IgG2a class are capable of activating serum complement upon binding to the target cells which express the cognate antigen.

In general, antibodies of the IgG2a and IgG3 subclass and occasionally IgG1 can mediate ADCC, and antibodies of the IgG3, IgG2a and IgM subclasses bind and activate serum complement. Complement activation generally requires the binding of at least two IgG molecules in close proximity on the target cell. However, the binding of only one IgM molecule activates serum complement.

The present invention is based, in part, upon the discovery that the effectiveness of tumor cell lysis mediated by a particular antibody subclass varies depending upon the type of tumor antigen against which the antibody is directed. For example, we have identified several mouse IgG3 and IgG2a antibodies directed against tumor cell surface glycolipid antigens which can mediate the killing of the human tumor cells in the presence of either human serum as a source of complement or human lymphocytes as a source of effector cells. By contrast, antibodies of the same subclass which are directed against protein antigens on the same tumor cells are ineffective.

The ability of any particular antibody to mediate lysis of the tumor cell target by complement activation and/or ADCC can be assayed using the test systems described in the examples herein. Accordingly, the tumor cells of interest can be grown and labeled in vitro; the antibody is added to the tumor cell culture in combination with either serum complement or with lymphocytes which may be activated by the antigen antibody complexes. Cytolysis of the target tumor cells is detected by the release of label from the lysed cells. In fact, antibodies can be screened using the patient's own serum as a source of complement and/or lymphocytes. The antibody that is capable of activating complement or mediating ADCC in the in vitro test can then be used therapeutically in that particular patient.

Antibodies of virtually any origin can be used according to the present invention provided they define a tumor-associated glycolipid antigen and can activate complement or mediate ADCC. Monoclonal antibodies offer the advantage of a continuous, ample supply. In fact, by immunizing mice with tumor-associated glycolipid antigens establishing hybridomas making antibodies to such antigens and selecting hybridomas making antibodies which can lyse tumor cells in the presence of human complement, using procedures similar to those described herein, it should be possible to rapidly establish a panel of antibodies capable of reacting with and lysing a large variety of human tumors.

While the invention is demonstrated using mouse monoclonal antibodies, the invention is not so limited; in fact, human antibodies may be used and may prove to be preferable. Such antibodies can be obtained by using human hybridomas (Cote et al., 1983, Proc. Natl. Acad. Sci, 80: 2026-2030) or by transforming human B cells with EBV virus in vitro (Cole et al., 1985, in, Monoclonal Antibodies and Cancer Therapy, Alan R. Liss, pp. 77-96). In fact, according to the invention, techniques recently developed for the production of "chimeric antibodies" (Morrison et al., 1984, Proc. Natl. Acad. Sci, 81: 6851-6855; Neuberger et al., 1984, Nature 312: 604-608; Takeda et al., 1985, Nature 314: 452-454) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention, as long as they specify cell surface glycolipid antigens and can mediate ADCC with human effector cells and/or activate human complement.

4.2. Therapeutic Uses of the Antibodies

The methods of the present invention can be used to apply antibodies for the therapy of tumors by administering the native antibody in an amount sufficient to cause reduction of the tumor by lysis of the tumor cells whether the mechanism be complement activated lysis or ADCC.

The selection of an antibody subclass for therapy will depend upon the nature of the tumor antigen. For example, an IgM may be preferred in situations where the glycolipid antigen is highly specific for the tumor target and rarely occurs on normal cells. However, where the tumor-associated antigen is also expressed in normal tissues, albeit at much lower levels, the IgG subclass may be preferred for the following reason: since the binding of at least two IgG molecules in close proximity is required to activate complement, less complement mediated damage may occur in the normal tissues which express smaller amounts of the antigen and, therefore, bind fewer IgG antibody molecules. Furthermore, IgG molecules by being smaller may be more able than IgM molecules to localize to tumor tissue.

There is evidence that complement activation in vivo leads to a variety of biological effects, including the induction of an inflammatory response and the activation of macrophages (Unanue and Benecerraf, 1984, Textbook of Immunology, 2nd Edition, Williams & Wilkins, Ch. 12 pp. 218-238). Tumor cells are more sensitive to a cytolytic effect of activated macrophages than are normal cells (Fidler and Poste, 1982, Springer Semin. Immunopathol. 5: 161-174. The increased vasodilation accompanying inflammation may increase the ability of various anti-cancer agents, such as chemotherapeutic drugs, radiolabelled antibodies etc., to localize in tumors. Therefore, antigen-antibody combinations of the type specified by this invention can be used therapeutically in many ways and may circumvent many of the problems normally caused by the heterogeneity of tumor cell populations (since antigen negative cells can also be killed using the approach of this invention). Additionally, purified glycolipid antigens (Hakomori, 1984, Ann. Rev. Immunol. 2: 103–126) or anti-idiotypic antibodies (Nepom et al., 1985, Proc. Natl. Acad. Sci. 81: 2864–2867; Koprowski et al., 1984, Proc. Natl. Acad. Sci. 81: 216–219) relating to such antigens could be used to induce an active immune response in human cancer patients. Such a response includes the formation of antibodies capable of activating human complement and mediating ADCC and by such mechanisms cause tumor destruction.

In the examples which illustrate the methods of the present invention four IgG3 antibodies, MG-21, 2B2,IF-4 and MG-23, which are specific for a GD3 ganglioside antigen expressed by cells from human melanoma and one IgG2a antibody, L6, which is specific for a ganglioside antigen expressed by cells from most human non-small cell lung carcinomas, breast carcinomas and colon carcinomas, can kill cells from the respective tumors in a short-term (2 or 4 hour $^{51}$Cr assay), if either complement is provided in the form of human serum or effector cells are provided in the form of human blood lymphocytes; three antibodies, MG-21, MG-23 and L6, both mediate ADCC and complement-dependent cytotoxicity. Antibodies to either of two melanoma-associated protein antigens, p97 and a proteoglycan, which are expressed on the cells used as targets with anti-GD3 antibodies failed to produce either ADCC or complement dependent cytotoxic reactions. Antibodies to protein antigens on those human lung carcinoma cells which also express the L6 antigen failed to mediate ADCC or complement dependent cytotoxicity. An IgG3 antibody mediating ADCC with human melanoma cells in the presence of mouse (or human) lymphocytes was able to destroy small transplants of human melanoma in nude mice, while antibodies not mediating ADCC when similarily tested could not. Serum from patients with cancer, even with diseminated cancer, could serve as a source of complement. Lymphocytes from patients with metastatic cancer did not mediate ADCC, but could be made to do so by exposure to T-cell growth factor. The combination of the right antibody (IgG2a or IgG3) and the right antigen (cell surface glycolipid) can make possible an effective killing of tumor cell; this mechanism, as well as other mechanisms related to an antibody's ability to mediate ADCC or activate human complement, can be used as a basis for the development of human tumor therapy.

4.2.1. Treatment of Melanoma

Four IgG3 antibodies, 2B2, IF4, MG-21 and MG-23 are described that bind strongly to a human melanoma-associated GD3 antigen. They mediate ADCC when combined with human effector cells, and two of the antibodies, MG-21 and MG-23, kill melanoma cells in the presence of human serum as a source of complement. Antibody 2B2, which gives ADCC also with mouse effector cells, was found to inhibit the outgrowth of a human melanoma in nude mice. Although most other antitumor antibodies which have been described in the literature lack these characteristics irrespective of their antigenic targets, an antibody to a proteoglycan antigen of melanoma cells described by Schultz et al. (1983, Proc. Natl. Acad. Sci. USA 80: 5407–5411), has been reported to have an antitumor effect that appears similar to that of 2B2.

High cytolytic activity was detected after 2 hours in $^{51}$Cr-release assays when human lymphocytes were combined with antibody and tested against cells expressing large amounts of the GD3 antigen; lymphocytes or antibodies alone were ineffective. Significant ADCC could be seen even at an antibody doses of 10 ng/ml and with one lymphocyte per target cell. The ADCC effect was antigen-specific, since cells lacking the GD3 antigen were not killed and the effect could be competitively inhibited by addition of antigen-positive tumor cells.

Antibody 2B2 gave significant ADCC also with mouse spleen lymphocytes as effectors, but antibody IF4 did not. This provided an impetus to investigate the antitumor activity of the two antibodies in mice grafted with a human melanoma expressing high levels of the GD3 antigen. Antibody 2B2 effectively prevented tumor outgrowth in most of the treated mice, whereas antibody IF4 gave no tumor inhibition. However, we cannot conclude from the present data that the in vivo effect of antibody 2B2 operates via ADCC; it could conceivably have other mechanisms, including direct antibody effects on tumor cells (Dippold et al.. 1983, Cancer Res. 44: 806–910) and macrophage activation.

Since antibody 2B2 could destroy small (1 mm diameter) tumor implants in nude mice and its ADCC activity was greater in the presence of human rather than mouse lymphocytes, one may speculate that it also might destroy small melanoma implants (in the form of micrometastases) in man. This, if true, may have therapeutic applications in patients who have deeply penetrating primary melanomas and, therefore, poor prognosis. Studies on patients with advanced melanoma (as normally chosen for pilot trials) are complicated by the fact that lymphocytes from most such patients do not give significant ADCC. However, an ADCC was detected when the lymphocytes from these patients were first exposed to T-cell growth factor.

Antibodies 2B2, IF4 and MG-21 are also described in Hellstrom et al., 1985, Proc. Natl. Acad. Sci. USA 82: 1499–1502 which is incorporated by reference herein. The MG-21 antibody is also described in U.S. application Ser. No. 834,162 filed Feb. 20, 1986 (allowed), which is incorporated by reference herein in its entirety.

4.2.2. Treatment of Carcinoma

An IgG2a antibody, L6, is described that is highly specific for a ganglioside antigen expressed by cells from most human non-small cell lung carcinomas, breast carcinomas and colon carcinomas. The L6 antibody and the antigen it defines are described more fully in U.S. Pat. No. 4,935,495 issued June 19, 1990 and U.S. Pat. No. 4,906,562 issued March 6, 1990 each of which is incorporated by reference herein in its entirety.

The L6 antibody can mediate ADCC of the tumor target cells in the presence of human lymphocytes or macrophages. In addition, the L6 antibody can activate complement upon binding to the target tumor cell in the presence of human serum. Thus, the L6 antibody could be administered in vivo for the therapy of lung, breast and/or colon carcinomas.

5. PREPARATION OF MONOCLONAL ANTIBODIES

The subsections below describe how the antibodies used in the examples which follow were prepared.

The binding assays used to characterize the specificity of the antibodies were performed by using radiolabeled antibodies (Brown et al., 1981, Proc. Natl. Acad. Sci. 78: 539–543); cultured cells ($10^6$) were incubated at 4° C. for 30 minutes with $10^6$ cpm of $^{125}$I-labelled antibody in 100 μl of heat-inactivated (30 minutes at 56° C.) fetal calf serum in culture medium. After the addition of 5 ml of PBS, the cells were pelleted by centrifugation for 10 minutes at 250×g. The supernatant was aspirated and the pellet was assayed for $^{125}$I. To measure nonspecific binding, parallel incubations were performed with 10 μg of unlabeled antibody as a competitor (Brown et al., 1981, Proc. Natl. Acad. Sci. 78: 539–543). In some instances binding assays were carried out in an analogous fashion on cell monolayers attached to plastic culture dishes.

5.1. Monoclonal Antibodies Directed Against Melanoma Glycolipids

In order to prepare antibodies directed against tumor-associated glycolipid antigens of melanoma cells, BALB/c mice were immunized with a melanoma cell line, SK-MEL-28, and their spleen cells subsequently were hybridized with NS-1 cells. Hybridoma supernatants were screened for binding to GD3 that had been isolated from melanoma tissue and attached to the surface of the wells of Falcon 3034 Microtest plates as previously described (Yeh et al., 1982, Int. J. Cancer 29: 269–275). Irrelevant gangliosides were included as controls. Hybridomas 2B2 and IF4 were derived from one hybridization, and hybridoma MG-21, from a different one. MG-23 is an antibody that has characteristics similar to those of MG-21. They were cloned twice by limiting dilution; all make antibodies that are IgG3 according to gel diffusion.

For comparison, two different antibodies, 96.5 and 48.7, were used. The former is an IgG2a antibody directed against p97, a melanoma associated glycoprotein of $M_r$97,000 (Woodbury et al., 1980, Proc. Natl. Acad. Sci. USA 77: 2183–2186; Brown et al., 1981, J. Immunol. 127: 539–546), and the latter is an IgG2b antibody specific for a proteoglycan antigen expressed by most melanomas (Hellstrom et al., 1983, J. Immunol. 130: 1467–1472). These antibodies have not, in previous experiments, given significant ADCC or inhibition of human melanomas in nude mice.

Antibodies were affinity-purified on a column of staphylococcal protein A covalently linked to Sepharose CL-4B (Pharmacia) by elution with 0.1 M citrate buffer, pH 3.5 or 4.5 (Brown et al., 1981, J. Immunol. 127: 539–546).

Antibody specificity for melanoma was established by binding assays with cultured cells, as published for antibody 4.2. (Yeh et al., 1982, Int. J. Cancer 29: 269–275; Nudelman et al., 1982, J. Biol. Chem. 257: 12752–12756). Specificity was confirmed by immunohistological studies on frozen section (Garrigues et al., 1982, Int. J. Cancer 29: 511–515), in which antibodies 2B2, IF4, and MG-21 stained samples from approximately 80% of metastatic melanomas, whereas normal tissues, including kidney and brain, were not stained; the specificity data for 2B2 have been published (Hellstrom et al., 1984, Contributions to Oncology Series: Genes and Antigens in Cancer Cells, eds. Riethmuller, G., Koprowski, H., Van Kliest, S. & Munk, K. (Karger, Basel), pp. 121–131.

5.2. Monoclonal Antibodies Directed Against Non-small Cell Lung Carcinoma Glycolipid The L6 monoclonal antibody was prepared as previously described in U.S. Pat. No. 4,935,495 issued June 19, 1990 and U.S. Pat. No. 4,906,562 issued March 6, 1990 each of which is incorporated by reference herein in its entirety. The preparation of monoclonal antibody L6 is described briefly below.

Monoclonal antibodies were produced by immunizing three-month-old BALB/c mice with explanted cells from a human adenocarcinoma of the lung, 2981. The immunization was performed by injecting the mice intraperitoneally 4 times with approximately $10^7$ cells. Three days after the last immunization, the spleens were removed suspended in culture medium and fused with NS-1 mouse myeloma cells (Kohler and Milstein, 1975, Nature 256: 495–497). The mixtures were seeded to form low density cultures originating from single fused cells (clones); the techniques used for the hybridization have been previously described by Yeh et al., (1982, Int. J. Cancer 29: 269–275).

Supernatants from hybrid cells were screened by using both an ELISA assay and an autoradiographic indirect $^{125}$I-labeled protein A assay (Brown et al., 1979, J. Immunol. Meth. 31: 201–209) against extracts from the tumors used for immunization which contained, inter alia, cell membranes. These extracts were prepared using a procedure modified from Colcher et al. (1981, Cancer Res. 41: 1451–1459; Yeh et al., 1982, Int. J. Cancer 29: 269–275). To prepare the extracts tissues were washed and suspended with PBS; for intact tumors this was done by pressing through a stainless steel screen. After this, 1 mM NaHCO$_3$ containing 1 mM phenylmethylsulfonylfluoride (Calbiochem-Behring Corp., San Diego, Calif.) was added, and the material was then homogenized on ice. After centrifugation for 15 minutes at 27,000×g, the supernatant was removed, and the pellet was resuspended in PBS, sonicated for 1 minute, and stored at −70° C.

Hybridomas which produced antibodies binding to the cell membrane extracts were cloned, expanded in vitro, and further tested for antibody specificity. This testing was carried out by using an immunohistological technique (Garrigues et al., 1982, Int. J. Cancer, 29: 511–515), in which the ability of the antibodies to bind to frozen sections of lung carcinomas, other tumors and normal human tissues were tested. Those hybridomas which produced antibody of apparent specificity for human lung cancer were recloned, expanded and injected into pristane-primed three-month old BALB/c mice, where they grew as ascites tumors.

Antibodies secreted into the ascites were purified on protein A Sepharose (Ey et al., 1979, Immunochemistry, 15: 429–436) or by gel filtration in Sephacryl S-300. Purified antibodies were used for further characterization which included additional specificity tests by immunohistology, binding assays on intact cells to determine which antibodies bound to the cell surface, and by radioimmunoprecipitation tests.

Monoclonal antibody L6 was produced from the corresponding hybridoma as described above.

6. ASSAYS USED TO CHARACTERIZE THE MONOCLONAL ANTIBODIES

6.1. Isotype Determination

Two techniques were used to determine isotypes, Ouchterlony immuno-diffusion and an assay carried out in 96-well plates.

For Ouchterlony immunodiffusion, an aliquot of supernatant of particular hybridoma cells was placed into the center well of a 2% agar plate. Mono-specific rabbit anti-mouse Ig isotypes antibodies (Meloy Lab, Springfield, VI) were placed in the outer wells and plate was incubated for 2 hours at room temperature and overnight at 4° C.

Flexible polyvinylchloride 96 well plates (Costar) were coated with 0.1 mg/ml goat anti-mouse Ig antibodies for 2 hours at 37° C. and countercoated with a 3% BSA solution for 2 hours at 37° C. The hybridoma supernatant was then incubated at 37° C. for 2 hours. After washing with PBS, bovine serum albumin (BSA) plates were incubated at 37° C. for 2 hours with monospecific rabbit anti-mouse Ig isotype antibodies coupled to peroxidase (Zymed, South San Francisco, Calif.). After washing, plates were incubated with 1 mg/ml orthophenylenediamine and 0.03% $H_2O_2$ in 0.1 M citrate buffer pH 4.5. Optical density at a wavelength of 630 nm was determined on a Dynatec ELISA plate reader.

6.2. Antibody-dependent Cellular Cytotoxicity Assay

A short-term $^{51}$Cr-release test was used to detect ADCC of target tumor cells (Cerrotini et al, 1974, Adv. Immunol. 18: 67–132). Peripheral blood lymphocytes from five healthy human subjects were separated on Ficoll-Hypaque (Hellstrom et al., 1981, Int. J. Cancer 27: 281–285) to provide effector cells and were pre-screened for low (less than or equal to 10%) natural killer cell reactivity against SK-MEL-28 cells; unless indicated otherwise the ratio of lymphocytes to target cells was 100:1. Spleen lymphocytes from normal BALB/c mice were also included in two tests. Target cells ($10^6$) were labeled by incubation with 100 $\mu$Ci(1 Ci=37 GBq) of $^{51}$Cr for 2 hours at 37° C., after which they were washed three times and resuspended in medium. The labeled cells were seeded ($2\times 10^4$ cells per well in 20 $\mu$l) into Microtiter V-bottom plates (catalog no. 1-220- 25X, Dynatech Laboratories, Alexandria, Va.). Purified antibody (100 $\mu$l per well) then was added, followed by $2\times 10^5$ lymphocytes per well in 100 $\mu$l; experiments with lower numbers of lymphocytes per well and with lower antibody concentrations also were carried out. The mixtures were incubated for 2 or 4 hours (See Tables and text), after which the plates were centrifuged at 400×g. The supernatants were removed and the radioactivity in 100 $\mu$l samples was measured with a $\gamma$-counter. There were two replicates per group; the variation between replicates was always less than 10%. Spontaneous release was defined as the cpm released into the medium from target cells that were osmotically lysed at the end of the assay. Percent cytotoxicity was calculated as $$\frac{\text{experimental group release} - \text{spontaneous release}}{\text{total release} - \text{spontaneous release}} \times 100$$

6.2.1. Isolation of Lymphocytes and Characterization of Effector Cells

Two types of donors of human blood lymphocytes and sera were tested. First, we used healthy, adult human subjects, 25–45 years of age. Second, we tested patients with melanoma. After the blood samples were drawn using 20 units heparin/ml of blood, lymphocytes were separated on Ficoll-Hypaque (Hellstrom et al., 1981, Int. J. Cancer 27: 281–285).

Most tests were done on lymphocytes frozen in a mixture of 10% dimethylsulfoxide (DMSO), 20% fetal calf serum and RPMI culture medium (Grand Island Biological Company, Grand Island, N.Y.) as previously described (Hellstrom et al., 1981, Int. J. Cancer 27: 281–285) and were thawed at 37° C. prior to testing.

In order to characterize the effector cells, tests were performed in which lymphocyte preparations obtained by separation on Ficoll-Hypaque were incubated for 1 hour at 37° C. in plastic culture flasks to remove adherent cells, after which they were passed through a nylon wool column (Julius et al., 1973, Eur. J. Immunol. 3: 645–649); the cells in the column effluents were used as a source of effector cells. In other tests, the Ficoll-Hypaque-purified lymphocytes were incubated for 1 hour at 37° C. with a mixture of anti-Leu-llb antibody (Becton-Dickinson, Mt. View, Calif.) at a concentration of 0.1 $\mu$g/$10^6$ lymphocytes and rabbit serum diluted 1:5 (as a source of complement1; this was done in order to abolish reactivity mediated by natural killer (NK) cells (Thompson et al., 1982, American Association for Clinical Histocomp. Testing, 8th Annual Meeting, p. A23).

6.2.2. Treatment of Lymphocytes With T-cell Growth Factor

Peripheral blood lymphocytes ($10^6$/ml) were treated with T-cell growth-factor by incubating the lymphocytes in vitro for 5 days in the presence of 10% human T-cell growth factor (TGF, Cellular Products, Inc., Buffalo, N.Y.) 20% human AB serum and 70% RPMI culture medium.

6.2.3. Target Cells

Five different human melanoma lines from metastatic melanoma were used. All except one, M-2634, express high levels of the GD3 antigen according to binding assays, which were carried out as previously described (Yeh et al., 1982, Int. J. Cancer 29: 269–275; Nudelman et al., 1982, J. Biol. Chem. 257: 12752–12756). Four of the lines, SK-MEL-28 (Woodbury et al., 1980, Proc. Natl. Acad. Sci. USA 77, 2183–2186), M-2669 clone 13, M-2634, and M-2765, were propagated in vitro. The fifth line, M-2586, failed to grow in vitro and so was serially transplanted in nude mice, were it grew better than any of the other lines. Human lung (bronchial) carcinoma line CH27 was used as a control for antibody specificity. It does not express detectable GD3 antigen.

6.3. Complement Mediated Cytotoxicity Assay

The $^{51}$Cr-release assay also was used to test the ability of antibodies to kill melanoma cells in the presence of human serum as a source of complement. It was carried out similarly to the assays for ADCC, except that 100 $\mu$l of undiluted unheated human serum was added per microtest well, instead of a suspension of effector cells; this serum was derived from normal human subjects.

6.4. Test of Antibody Activity In Vivo

Athymic nude (nu/nu) two- to three-month-old male mice were obtained from Charles River Breeding Laboratories and housed in filter-top cages (five mice per cage) placed in condominium units.

The mice were grafted subcutaneously on both flanks with a small piece ($1\times 1$ mm diameter) of melanoma M-2586, which expresses both p97 (Woodbury et al., 1980, Proc. Natl. Acad. Sci. USA 77: 2183–2186) and the GD3 antigens (Yeh et al., 1982, Int. J. Cancer 29: 269–275). Each experimental group comprised 5 mice. This represented 10 "sites," since the mice were grafted on both sides. The control group had 10 mice (20 sites).

On the day after grafting and on each third day thereafter, the mice were injected via the tail vein with 1 mg of antibody in phosphate-buffered saline; this dose was chosen to provide excess antibody in the treated mice. Separate groups received antibody 2B2, IF4, or 96.5 or a combination of the three; the last group was injected with one-third of the dose of each antibody A total of six antibody injections were given, at 3-day intervals. The control group was injected with equivalent volumes of culture medium at the same times.

The mice were inspected three times weekly over a period of 6 months. by the end of the 6 months, all the control mice had died from tumor. At each inspection, two perpendicular diameters of each palpable tumor were measured, and mean tumor diameters (±SE) were calculated; a tumor is considered palpable herein when its mean diameter is greater than or equal to 2 mm. The data are presented as number of sites with palpable tumor per group out of the total number of sites injected.

7. Monoclonal Antibody MG-21

Hybridoma MG-21 was derived from one hybridization of mouse spleen cells from mice immunized with the human melanoma cell line SK-MEL-28 as described in Section 5.1. The monoclonal antibody MG-21 is an IgG3 antibody directed against the GD3 antigen of human melanoma. The following subsections describe the results of various assays which demonstrate the ability of antibody MG-21 to induce ADCC and/or complement mediated killing of melanoma cells. MG-23 has characteristics similar to that of MG-21.

7.1. Antibody Dependent Cellular Cytotoxicity Assay

In the first set of experiments the M-2669 cell line, which are human melanoma cells expressing more than 100,000 molecules per cell of GD3 ganglioside antigen, were incubated with purified MG-21 and peripheral blood lymphocytes from a normal human subject. The data presented in Table I indicate that significant killing of the melanoma target cells was observed. In fact, significant killing of the melanoma target cells was observed even at a small antibody concentration (1 µg/ml) and a low lymphocyte to target cell ratio (10:1). By contrast, lymphocytes alone, the MG-21 antibody alone, or lymphocytes incubated with either antibody 96.5 which is directed against p97, a rumor-associated protein antigen, and antibody 48.7 directed against a proteoglycan also expressed strongly by the same melanoma cells, did not cause significant release of isotope.

TABLE I

ADCC against M-2669 Melanoma Cells as Targets With Human Lymphocytes Combined with Antibody MG-21 or Control Antibodies 96.5 and 48.7

| RATIO Human Lymphocytes Per Target Cell | % Cytotoxicity of M-2669 Target Cells | | |
|---|---|---|---|
| | MG-21 (µg/ml) 10 1 | 96.5 (µg/ml) 10 | 48.7 (µg/ml) 10 |
| 100 | 82  76 | 0 | 0 |
| 10 | 64  52 | ND | ND |
| 1 | 14  13 | ND | ND |

Cytotoxicity was determined in 4-hr $^{51}$Cr-release assay. Antibodies alone gave no cytotoxicity and lymphocytes alone gave less than or equal to 5% cytotoxicity. ND, not done.

The results in Table II show that incubation of the lymphocytes from normal subjects with anti-Leu-llb antibody and complement abolished the ability of the lymphocytes to lyse the target cells (i.e., to mediate ADCC) in the presence of MG-21. This indicates that the lymphocytes had the characteristics of natural killer (NK) cells (Thompson et al., 1982, Am. Assoc. for Clinical Histocompatibility Testing, 8th Annual Meeting, p. A23).

TABLE II

Inhibition of ADCC against M-2669 Melanoma Cells by Incubation of Lymphocytes from a Normal Subject with Anti-Leu-11b Antibody and Complement

| Treatment of Lymphocytes | % Cytolysis* | |
|---|---|---|
| | Lymphocytes alone | Lymphocytes + MG-21 (10 µg/ml) |
| None (culture medium) | 3 | 24 |
| Complement | 3 | 22 |
| Anti-Leu-11b and Complement | 2 | 2 |

*10 lymphocytes per target cell

In view of the interest in developing therapy for human cancer, the next step was to investigate whether lymphocytes from patients with disseminated metastases could serve as effector cells in the ADCC assays, since these patients would most likely be the first candidates for therapeutic trials. As shown in Table III, lymphocytes from such patients failed to mediate significant ADCC. However, significant killing by lymphocytes alone and an even greater killing by lymphocytes and MG-21 antibody was observed, if the lymphocytes were first incubated with a preparation containing a T-cell growth factor for 5 days; see Table IV.

TABLE III

ADCC against M-2669 Melanoma Cells and Lymphocytes from Normal Subjects or Melanoma Patients Combined With Antibody MG-21

| Human Lymphocyte Doner | % Cytotoxicity of M-2669 Target Cells | |
|---|---|---|
| | No Antibody | MG-21 |
| Normal Subjects | | |
| N-1 | 6 | 51 |
| N-3 | 6 | 55 |
| Stage IV Melanoma | | |
| M-3 | 4 | 2 |
| M-5 | 3 | 7 |
| Stage I Melanoma | | |
| M-2 | 0 | 31 |

100 effector cells (lymphocytes)/target cell (M-2669) and 50 µg/ml MG-21.

TABLE IV

NK Activity and ADCC against M-2669 Melanoma Cells and Lymphocytes Incubated In Vitro with T-Cell Growth Factor (IL-2) for 5 Days Prior to Combining them with Antibody MG-21 and Target Cells

| Lymphocytes Donor | Ratio to Target Cell | MG-21 (µg/ml) | % Cytotoxicity of M-2669 Target Cells | |
|---|---|---|---|---|
| | | | Lymphocytes Un-Treated | TCGF Treated |
| Stage IV Prostate Carcinoma | 10 | 0 | 0 | 20 |
| | | 10 | 6 | 36 |
| Stage II Breast Carcinoma | 10 | 0 | 2 | 68 |
| | | 10 | 25 | 85 |
| | 1 | 0 | 2 | 29 |
| | | 10 | 11 | 55 |

7.2. Complement-mediated Cytotoxicity Assay

The cytotoxicity of antibody MG-21 to GD3-positive melanoma cells in the presence of human serum as a source of complement was determined using a 4-hr $^{51}$Cr-release assay similar to the ADCC assay but adding undiluted unheated human serum instead of lymphocytes. As shown in Tables V and VI antibody MG-21 gave a strong cytotoxic effect in the presence of human serum. Heat inactivation (56° C. for 30 minutes) of the human serum abolished its effect.

The results in Table V demonstrate that up to 100% of the target cells were lysed when antibody MG-21 and human serum were both added. Antibody MG-21 alone and human serum along had no cytolytic effect on the melanoma cell, and inactivating the complement abolished the cytolytic effect.

TABLE V

Lysis of Tumor Cells by Antibody MG-21 In the Presence of Unheated Human Serum as a Source of Complement

| Target Cells | GD3 Expression | Complement | MG-21 (μg/ml) | % Cytotoxicity |
|---|---|---|---|---|
| SK-MEL-28 | +++ | Inactive | 50 | 0 |
|  |  | Active | 50 | 30 |
|  |  |  | 10 | 2 |
|  |  |  | 1 | 0 |
| M-2669 | +++ | Active | 50 | 100 |
|  |  |  | 10 | 58 |
|  |  |  | 1 | 2 |
| M-2765 | +++ | Active | 50 | 100 |
|  |  |  | 10 | 77 |
| H-3021 | − | Active | 50 | 0 |
|  |  |  | 10 | 0 |
| H-2722 | − | Active | 50 | 1 |
|  |  |  | 10 | 3 |

Cytotoxicity determined in a 4 hr $^{51}$Cr release assay. Cell lines H-3021 and H-2722 are non-melanomas which do not express detectable amounts of the GD3 antigen The results in Table VI demonstrate that by contrast to MG-21, antibodies 96.5 and 48.7 which are specific for melanoma-associated antigens that are strongly expressed in the M-2669 cells, p97 glycoprotein and a proteoglycan, respectively, failed to kill the M-2669 target cell in the presence of complement.

TABLE VI

Complement Mediated Lysis of M-2669 Target Cells by MG-21 Directed Against GD3 Melanoma Antigen as Compared to that of Antibodies Directed Against Melanoma-Associated Protein Antigens

| | % Complement Dependent Lysis of M-2669 Target Cells Antibody Concentration (μg/ml) | |
|---|---|---|
| Antibody | 50 | 10 |
| MG-21 | 64 | 24 |
| 96.5 | 3 | 2 |
| 48.7 | 1 | 7 |

Antibody 96.5 is specific for p97 a melanoma-associated glycoprotein antigen and antibody 48.7 defines a melanoma-associated proteoglycan antigen; both of which are also strongly expressed on the surface of M-2669 target cells.

In view of the interest in developing therapy for human cancer, the next step was to investigate whether serum from patients with disseminated metastases could serve as an adequate source of complement with antibody MG-21. The results in Table VII demonstrate that the complement dependent cytotoxicity of MG-21 was even slightly greater with serum derived from a patient with Stage IV melanoma than with serum from a normal subject.

TABLE VII

Complement Dependent Lysis of M-2669 Target Cells by Antibody MG-21 in the Presence of Serum from a Normal Human Subject or a Patient with Stage IV Melanoma

| | % Complement Dependent Lysis of M-2669 Cells MG-21 Concentration (μg/ml) | | |
|---|---|---|---|
| Serum Donor | 50 | 10 | 1 |
| Normal | 79 | 57 | 0 |
| Stage IV Melanoma M-7 | 83 | 64 | 0 |

Percentage cytotoxicity statistically differenct from 0, with p less than or equal to 0.01. No cytotoxicity was observed when antibody or serum alone were assayed.

8. MONOCLONAL ANTIBODY 2B2

Hybridomas 2B2 and IF4 were each derived from one hybridization of spleen cells from mice immunized with the human melanoma cell line SK-MEL-28 as described in Section 5.1. The monoclonal antibody 2B2 is an IgG3 antibody directed against the GD3 antigen of human melanoma. The following subsections describe the results of various assays which demonstrate the ability of antibody 2B2 to induce antibody dependent cellular cytotoxicity of melanoma cells and to destroy small tumor implants in nude mice.

8.1. Antibody Dependent Cellular Cytotoxicity Assay

In the first set of experiments human melanoma cell lines which express more than 100,000 molecules per cell of a GD3 ganglioside antigen were incubated with purified 2B2 and peripheral blood lymphocytes from either a normal human subject or from mice. The data presented in Table VIII indicates that significant killing was observed.

TABLE VIII

ADCC Against Tumor Cells as Targets and Lymphocytes Combined With Anti-GD3 Antibody 2B2

| Target Cell | Lymphocytes | | Antibody | | % Cytotoxicity |
|---|---|---|---|---|---|
|  | Donor | No./Target Cell | | (μg/ml) | |
| SK-MEL-28 (GD3+) | Human | 100 | 2B2 | 10.0 | 37 |
|  |  |  |  | 1.0 | 31 |
|  |  |  |  | 0.1 | 20 |
|  |  |  |  | 0.01 | 8 |
|  |  |  |  | 0 | 5 |
|  |  | 0 |  | 10.0 | 0 |
|  |  | 100 | 48.7 | 10.0 | 0 |
|  | Mouse | 100 | 2B2 | 10.0 | 21 |
|  |  |  |  | 0 | 1 |
|  |  | 0 |  | 10.0 | 1 |
|  |  | 100 | IF4 | 10.0 | 4 |
| M-2669 (GD3+) | Human | 100 | 2B2 | 10.0 | 68 |
|  |  |  |  | 1.0 | 50 |
|  |  | 10 |  | 10.0 | 40 |
|  |  |  |  | 1.0 | 17 |
|  |  | 1 |  | 10.0 | 13 |
|  |  |  |  | 1.0 | 7 |
|  |  | 100 | 96.5 | 10.0 | 0 |
|  |  | 100 | 48.7 | 10.0 | 0 |
| CH27 (GD3−) | Human | 100 | 2B2 | 10.0 | 0 |
|  |  | 0 |  |  | 0 |
|  |  | 0 |  | 10.0 | 0 |

Cytotoxicity was determined in 3-hr $^{51}$Cr-release assay, except for assays in which M-2669 was the target cell in which case cytotoxicity was determined in 4-hr incubations.

By contrast, the lymphocytes alone, the 2B2 antibody alone or lymphocytes incubated with either antibody 96.5 which is directed against p97, a tumor-associated glycoprotein antigen and antibody 48.7 directed against a proteoglycan also expressed strongly by the same melanoma cells and did not cause significant release of isotope. Antibody 2B2 and lymphocytes had no effect on target cells from a control tumor, CH27, which does not express the GD3 antigen. Antibody 2B2 also gave significant ADCC with mouse spleen lymphocytes as effectors, but antibody IF4 did not.

The ADCC activity of antibody 2B2 was evaluated in the presence of lymphocytes from five different normal donors. As shown in Table IX, effector cells from each of the donors gave strong ADCC.

TABLE IX

ADCC Against M-2669 Cells as Targets and Lymphocytes from Normal Subjects Combined with Antibody 2B2

| Normal Human Lymphocyte Donor | Cytotoxicity of M-2669 Target Cells Ratio of Lymphocyte: Target Cell | |
|---|---|---|
| | 100:1 | 10:1 |
| A | 82 | 50 |
| B | 55 | 26 |
| C | 64 | ND |
| D | 85 | ND |
| E | 88 | ND |

Cytotoxicity was determined in a 4-hr $^{51}$Cr-release assay. Antibody alone gave no cytotoxicity and lymphocytes alone gave less than or equal to 5% cytotoxicity. ND, not done It was also investigated whether lymphocytes from patients with disseminated metastases could serve as effector cells in the ADCC assay with antibody 2B2. As shown in Table X, lymphocytes from such patients failed to mediate ADCC. These data are similar to those given in Table III for MG-21.

TABLE X

ADCC Against M-2669 Cells as Targets and Lymphocytes from Normal Subjects of Melanoma Patients When Combined With Antibody 2B2

| Human Lymphocyte Donor | % Cytotoxicity of M-2669 Target Cells | |
|---|---|---|
| | No Antibody | 2B2 |
| Normal Subjects | | |
| N-1 | 6 | 34 |
| N-3 | 6 | 38 |
| Stage IV Melanoma | | |
| M-3 | 4 | 3 |
| M-5 | 3 | 5 |
| Stage I Melanoma | | |
| M-2 | 0 | 15 |

100 effector cells (lymphocytes)/target cell (M-2669) and 50 μg/ml 2B2.

8.2. Complement Mediated Cytotoxicity Assay

The cytotoxicity of GD3-positive melanoma in the presence of human serum as a source of complement was determined using a 4-hour $^{51}$Cr-release assay similar to the ADCC assay but adding undiluted unheated human serum instead of lymphocytes. Unlike antibody MG-21, antibody 2B2 gave no effect.

8.3. Antitumor Effects of Antibody 2B2 In Vivo

We tested whether antibodies 2B2 or IF4 had any antitumor effect in vivo. These antibodies were chosen because 2B2 but not IF4 gave ADCC with mouse effector cells (see Table VIII). Melanoma M-2586 was used as a target, since it grows extremely well in nude mice, expresses the GD3 antigen, can be used as a target for 2B2-mediated ADCC, and can competitively inhibit ADCC against SK-MEL-28 cells. M-2586 was grafted onto both flanks of nude mice, and the mice were injected with a dose of antibody expected to give a blood concentration exceeding that needed for ADCC in vivo. Anti-p97 antibody 96.5 was tested in parallel, as was a combination of all three antibodies (same total antibody concentration).

As shown in Table XI, antibody 2B2 almost completely supressed the outgrowth of melanoma grafts, with only 1 of 10 injected sites having a detectable tumor four months after grafting, as compared to 19 of 20 sites in the control. The small implanted tumor pieces thus had been rejected at all 10 sites in the 2B2 group except for one. Six months after grafting, 4 mice in the 2B2 group survived, tumor-free, but all the controls were dead with large (greater than 15-mm diameter) tumors. Neither antibody 96.5 nor antibody IF4 inhibited tumor outgrowth. The group receiving a combination of antibodies 2B2, IF4, and 96.5 also showed inhibition, with 3 of 10 sites developing progressively growing tumors.

The inhibition mediated by antibody 2B2 was statistically significant from 2 months after tumors were implanted whether the comparison with the control group was made on the basis of the number of sites with tumor, using a Fischer table (P less than 0.001), or on the basis of mean tumor diameters, using Student's t test (P less than 0.001).

TABLE XI

Antibody 2B2 Inhibits Outgrowth of Human Melanoma in Nude Mice

| Treatment | Sites with tumor/total number of sites | |
|---|---|---|
| | 2 months after transplant | 4 months after transplant* |
| Control (culture medium) | 18/20 | 19/20 |
| Antibody 2B2 (anti-GD3) | 1/10 | 1/10 |
| Antibody IF4 (anti-GD3) | 8/10 | 10/10 |
| Antibody 96.5 (anti-p97) | 9/10 | 10/10 |
| Combination (2B2, IF4, and 96.5) | 3/10 | 3/10 |

A 1 × 1 mm tumor piece (human melanoma M-2586) was grafted on each flank of nude mice. The next day and at five subsequent times, at 3-day intervals, they were injected intravenously with a 1 mg of antibody. There were 5 mice (10 sites) per group except for the control, which had 10 mice (20 sites).
*All mice were dead at 6 months after transplantation except for 4 of the 5 mice who received antibody 2B2 and 2 of the 5 mice who received the combination; these mice were all alive and tumor-free.

9. MONOCLONAL ANTIBODY L6

Hybridoma L6 was derived from one hybridization of spleen cells from mice immunized with a human adenocarcimona of the lung, 2981 as described in Section 5.2. The monoclonal antibody L6 is an IgG2a antibody directed against a ganglioside antigen expressed in large amounts at the surface of cells from non-small cell lung carcinoma and certain other tumors. The following subsections describe the results of various assays that demonstrate the ability of antibody L6 to induce antibody dependent cellular cytotoxicity and/or complement mediated killing of lung carcinoma cells expressing large amounts of the L6 ganglioside antigen.

9.1. Antibody Dependent Cellular Cytotoxicity Assay

The L6 antibody when combined with human lymphocytes mediates ADCC of target cells expressing large amounts of the L6 ganglioside antigen (above 100,000 molecules per cell), while target cells expressing little L6 antigen were not killed; see Table XII. Among the cell lines expressing much L6 antigen, cell line 2981 was a more sensitive target than line CH27. The effector cells were found to express the Leu-llb antigen, and therefore, are similar to the cells mediating ADCC of melanoma in the presence of MG-21. by contrast, antibodies directed to three protein antigens expressed by the target cell line 2981 could not mediate ADCC.

TABLE XII

ADCC of Antibody L6 as Assayed Against Different Target Cells

| Target Cell | Lymphocytes No./Target Cell | % Cytotoxicity of Target Human Cells with L6 Antibody μg/ml | | |
|---|---|---|---|---|
| | | 0 | 10 | 50 |
| CH27 (L6+) | 100 | 10 | 40 | 46 |
| | 0 | ND | ND | 0 |
| 2981 (L6+) | 100 | ND | 66–84* | ND |
| | 10 | 13 | 37 | 44 |
| | 1 | 2 | 10 | 10 |
| 2964 (L6−) | 100 | 2 | 13 | 12 |

Cytotoxicity determined in a 4-hr $^{51}$Cr-release assay.
*These results are based on five pools of L6 antibody which had the following toxicity values: 66, 74, 76, 83, 84.
ND, no data.

9.2. Complement-mediated Cytotoxicity Assay

The experiment in Table XIII demonstrates that antibody L6, in the presence of human serum as a source of complement, can lyse tumor cells expressing the L6 ganglioside antigen but not cells lacking the antigen; the latter cells, which were GD3 positive, were lysed by complement activated by the antibody MG-21 thus demonstrating that the complement used in the assay was not inactivated.

TABLE XIII

Cytotoxicity Activity of Antibody L6 In the Presence of Unheated Human Serum as a Source of Complement

| Target Cells | | Target Cell Treatment | | % Complement Dependent Cytotoxicity |
|---|---|---|---|---|
| Type | Antigen Expressed | Complement | Antibody (μg/ml) | |
| 2981 | L6 | + | L6 50 | 54 |
| | | | 10 | 43 |
| | | | 1 | 1 |
| | | | 0 | 3 |
| | | 0 | 50 | 1 |
| | | | 10 | 3 |
| | | | 0 | 0 |
| 2669 | GD3 | + | L6 50 | 0 |
| | | | 10 | 0 |
| | | | 0 | 0 |
| | | + | MG-21 50 | 79 |
| | | | 10 | 67 |
| | | 0 | 50 | 0 |
| | | | 0 | 0 |

Antibodies to three protein antigens expressed by the target cell line 2981 which was used in the experiments in Table XIII could not activate complement-dependent cytotoxicity; see Table XIV.

TABLE XIV

Comparison of Complement-Dependent Cytotoxicity of Several Antibodies Capable of Binding to Lung Carcimona Cell Line 2981

| Antibody (10 μg/ml) | % Complement Dependent Cytotoxicity of 2981 |
|---|---|
| L6 | 34 |
| L3 | 3 |
| L5 | 6 |
| L18 | 5 |

TABLE XIV-continued

Comparison of Complement-Dependent Cytotoxicity of Several Antibodies Capable of Binding to Lung Carcimona Cell Line 2981

| Antibody (10 μg/ml) | % Complement Dependent Cytotoxicity of 2981 |
|---|---|
| None | 1 |

Antibodies L3, L5 and L18 are directed against protein antigens expressed by 2981 cells.

10. DEPOSIT OF CELL LINES

The following cell lines have been deposited with the ATCC, Rockville, Md., and have been assigned the following accession numbers:

| Cell Line | Accession Number |
|---|---|
| MG-21 | HB 9011 |
| L6 | HB 8677 |

The present invention has been described in detail with particular reference to the above embodiments. It will be understood, however, that the present invention is not to be limited in scope by the embodiments disclosed or cell lines deposited which are intended as illustrations of aspects of the invention.

Indeed, various modifications of the invention in addition to those shown and described herein will become apparent to those skilled in the art from the foregoing description. Such modifications are intended to fall within the scope of the appended claims.

What is claimed is:

1. A method for treating a human melanoma comprising administering in vivo an effective dose of a monoclonal antibody having the epitote binding specificity and biological effector function demonstrated by monoclonal antibody MG-21 produced by the hybridoma deposited with the ATCC and assigned accession number HB-9011, in which the monoclonal antibody is directed against a GD3 glycolipid antigen expressed by the melanoma and which upon complexing with the GD3 antigen activates serum complement or mediates antibody dependent cellular cytotoxicity so that the melanoma cells are killed.

2. A method for treating a human glioma comprising administering in vivo an effective dose of a monoclonal antibody having the epitote binding specificity and biological effector function demonstrated by monoclonal antibody MG-21 produced by the hybridoma deposited with the ATCC and assigned accession number HB-9011, in which the monoclonal antibody is directed against a GD3 glycolipid antigen expressed by the glioma and which upon complexing with the GD3 antigen activates serum complement or mediates antibody dependent cellular cytotoxicity so that the glioma cells are killed.

3. A method for treating a tumor that expresses a GD3 glycolipid antigen comprising administering in vivo an effective dose of a monoclonal antibody having the epitote binding specificity and biological effector function demonstrated by monoclonal antibody MG-21 produced by the hybridoma deposited with the ATCC and assigned accession number HB-9011, in which the monoclonal antibody is directed against the GD3 glycolipid antigen expressed by the tumor and which upon complexing with the GD3 antigen activates serum complement or mediates antibody dependent cellular cytotoxicity so that the cells of the tumor are killed.

* * * * *